(12) United States Patent
Chamberlain et al.

(10) Patent No.: US 9,392,996 B2
(45) Date of Patent: Jul. 19, 2016

(54) HAND-HELD MEDICAL IMAGING SYSTEM WITH DEDICATED POWER SOURCE DEVICES AND ASSOCIATED APPARATUSES AND METHODS

(71) Applicant: FUJIFILM Sonosite, Inc., Bothell, WA (US)

(72) Inventors: Craig Chamberlain, Seattle, WA (US); Paul Danset, Kirkland, WA (US)

(73) Assignee: FUJIFILM SonoSite, Inc., Bothell, WA (US)

( * ) Notice: Subject to any disclaimer, the term of this patent is extended or adjusted under 35 U.S.C. 154(b) by 270 days.

(21) Appl. No.: 14/256,731

(22) Filed: Apr. 18, 2014

(65) Prior Publication Data
US 2015/0297192 A1  Oct. 22, 2015

(51) Int. Cl.
*A61B 8/14* (2006.01)
*A61B 8/00* (2006.01)
*A61B 8/13* (2006.01)

(52) U.S. Cl.
CPC ... *A61B 8/56* (2013.01); *A61B 8/13* (2013.01); *A61B 8/4427* (2013.01); *A61B 8/462* (2013.01)

(58) Field of Classification Search
CPC ........ A61B 8/13; A61B 8/4427; A61B 8/462; A61B 8/56
See application file for complete search history.

(56) References Cited

U.S. PATENT DOCUMENTS

| 2003/0078501 | A1 | 4/2003 | Barnes et al. | |
| 2004/0147971 | A1 | 7/2004 | Greatbatch et al. | |
| 2007/0239019 | A1 | 10/2007 | Richard et al. | |
| 2011/0055447 | A1 | 3/2011 | Costa et al. | |
| 2013/0330588 | A1* | 12/2013 | Ahn | H01M 2/1016 429/99 |

FOREIGN PATENT DOCUMENTS

JP  2003033350 A  2/2003

OTHER PUBLICATIONS

International Searching Authority, International Search Report and Written Opinion, PCT Application PCT/US2015/026529, mailed Jul. 15, 2015, 13 pages.

* cited by examiner

*Primary Examiner* — Mark Remaly (57) ABSTRACT

A portable ultrasound system having dedicated power source devices is disclosed herein. In one embodiment, a portable ultrasound system can include transducer electronics and a base unit having base-unit electronics configured to receive user input and to operate the transducer electronics to perform ultrasound scanning based on the user input. The portable ultrasound system further includes a first power source device configured to power the transducer electronics and a second power source device configured to power the base-unit electronics without powering the transducer electronics.

14 Claims, 9 Drawing Sheets

Fig. 5

HAND-HELD MEDICAL IMAGING SYSTEM WITH DEDICATED POWER SOURCE DEVICES AND ASSOCIATED APPARATUSES AND METHODS

TECHNICAL FIELD

The disclosed technology is related to medical imaging systems, and, in particular, some embodiments are related to portable ultrasound devices having a compact form factor and a user interface that facilitates hand-held operation.

BACKGROUND

Portable ultrasound imaging devices are used by anesthesiologists, emergency and critical care personnel, and other medical professionals. A portable ultrasound device can include a clamshell-type base unit having a handle for carrying the base unit. The base unit can fold open to a display and a keypad, and a user can connect an ultrasound transducer wand to the base unit to acquire and view ultrasound images on the display.

BRIEF DESCRIPTION OF THE DRAWINGS

FIG. 1A is an isometric top view.

DETAILED DESCRIPTION

The following disclosure describes various types of hand-held imaging systems and associated apparatuses and methods. Certain details are set forth in the following description and FIGS. 1A-5 to provide a thorough understanding of various embodiments of the disclosure. Other details describing well-known structures and systems often associated with ultrasound systems, however, are not set forth below to avoid unnecessarily obscuring the description of the various embodiments of the disclosure.

Many of the details and features shown in the Figures are merely illustrative of particular embodiments of the disclosure. Accordingly, other embodiments can have other details and features without departing from the scope of the disclosure. In addition, those of ordinary skill in the art will understand that further embodiments can be practiced without several of the details described below. Furthermore, various embodiments of the disclosure can include structures other than those illustrated in the Figures and are expressly not limited to the structures shown in the Figures. Moreover, the various elements and features illustrated in the Figures may not be drawn to scale.

In the Figures, identical reference numbers identify identical or at least generally similar elements. To facilitate the discussion of any particular element, the most significant digit or digits of any reference number refer to the Figure in which that element is first introduced. For example, element 110 is first introduced and discussed with reference to FIG. 1A.

Figure 1A:
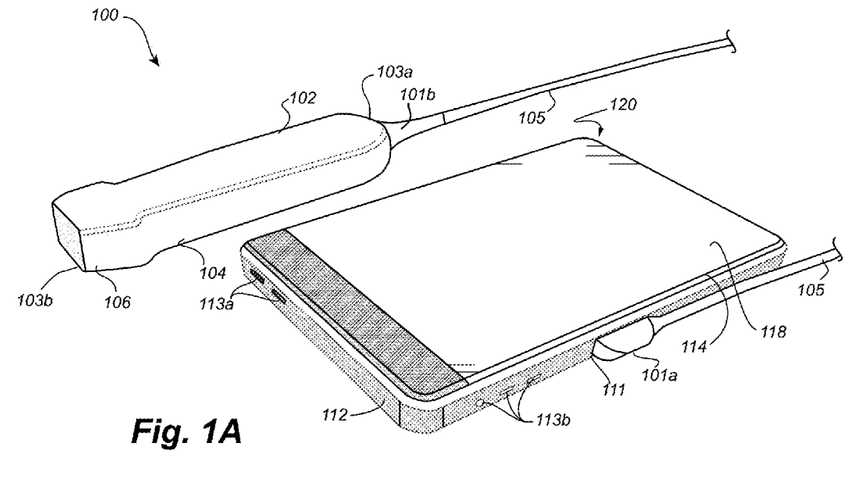
Figure 1B:
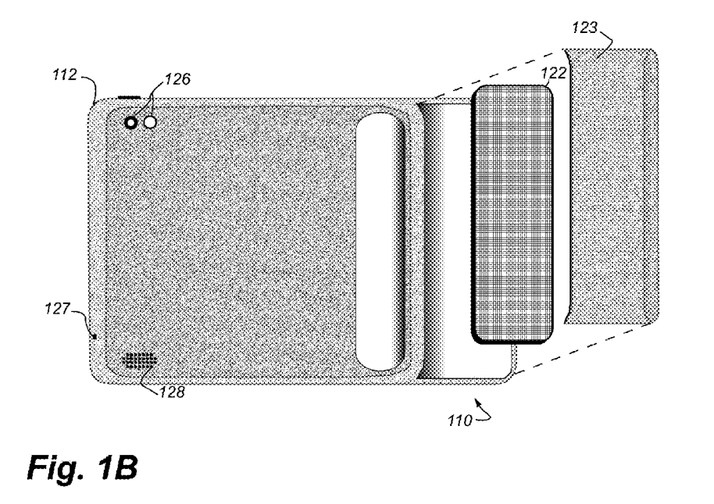
FIG. 1B is a partially-exploded bottom view of a portable ultrasound imaging system configured in accordance with an embodiment of the disclosure.

FIG. 1A is an isometric top view, and FIG. 1B is a partially-exploded bottom view of a portable ultrasound imaging system 100 ("portable system 100") configured in accordance with an embodiment of the disclosure. Referring to FIG. 1A, the portable system 100 includes an ultrasound transducer device or a transducer wand 102 operably coupled to a hand-held base unit 110 ("base unit 110") by a signal cable 105. The signal cable 105 has a first end 101a and a second end 101b connected between a wand port 111 of the base unit 110 and a proximal end portion 103a of the transducer wand 102. In some embodiments, the signal cable 105 can include a connector or plug at the second end 101b (not shown) configured to removably couple the signal cable 105 to the transducer wand 102.

The transducer wand 102 includes a housing 104 (e.g., a molded plastic housing) extending from the proximal end portion 103a to a distal end portion 103b. The housing 104 includes a scan head region 106 that encloses a transducer array (not shown) within the housing 104 toward the distal end portion 103b. In some embodiments, the transducer wand 102 can include one or more buttons, triggers, or other input devices (not shown) configured, for example, to toggle power on or off, put the portable system 100 in a standby state, or to perform other operations. In other embodiments, the transducer wand 102 can include, for example, light-emitting elements that visually indicate an operational state of the transducer wand 102, a housing having a different shape and/or size, and/or other configurations or features.

In the illustrated embodiment, the base unit 110 includes a casing 112 (e.g., a plastic and/or metallic casing) and a touchscreen display 114 ("touchscreen 114") attached to the casing 112. The touchscreen 114 can include a touchscreen surface 118 having transparent electrodes (e.g., indium tin oxide electrodes; not shown) in a capacitive configuration for sensing skin or stylus contact with the touchscreen surface 118. In another embodiment, the touchscreen surface 118 can include electrodes in a resistive configuration configured to sense pressure contact (rather than skin contact). In one aspect of this embodiment, a resistive configuration can enable a user to operate the touchscreen 114 with a gloved hand (e.g., a latex-gloved hand). The base unit 110 can also include user controls 113a and input/output (I/O) ports 113b at an outer edge of the base unit 110. The controls 113a can include, for example, buttons, knobs, switches, etc. The I/O ports 113b can include, for example, audio, universal serial bus (USB), high-definition multimedia interface (HDMI) ports), etc.

Referring to FIG. 1B, the base unit 110 can further include an internal cavity that defines a battery compartment containing a removable battery 122 (e.g., a rechargeable battery), which is covered by a removable battery cover 123. As further shown in FIG. 1B, the base unit 110 can also include cut-out sections 126-128 (e.g., apertures) for a camera, a microphone, and a speaker, respectively.

Figure 2A:
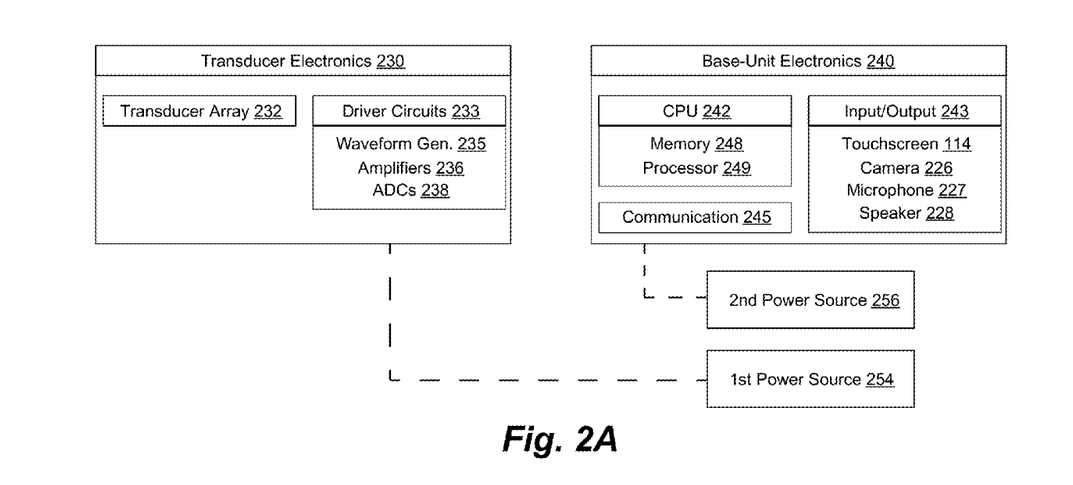
FIGS. 2A and 2B are schematic diagrams of various electronic components of a portable ultrasound system configured in accordance with an embodiment of the disclosure.
Figure 2B:
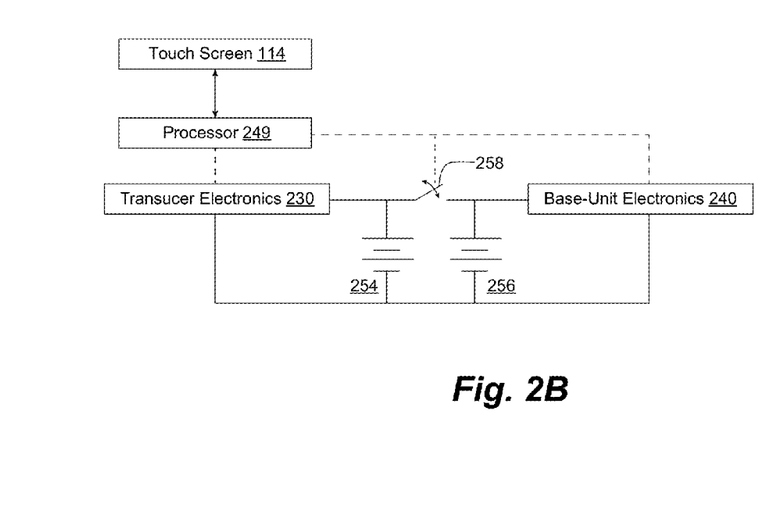

FIGS. 2A and 2B are schematic diagrams of various electronic components of the portable system 100 configured in accordance with an embodiment of the disclosure. Referring first to FIG. 2A, the portable system 100 includes transducer electronics 230 at the transducer wand 102 (FIG. 1A) and base-unit electronics 240 at the base unit 110 (FIG. 1A). The transducer electronics 230 can drive a transducer array 232, such as an array of microelectromechanical transducer elements, located at the scan head region 106 (FIG. 1A). The transducer electronics 230 can also include one or more driver circuits 233 configured to operate the transducer array 232. The driver circuits 233 can include, for example, waveform generators 235, amplifiers 236, analog to digital converts (ADCs) 238, and other ultrasound signal processing components (e.g., a CPU, controller, transmit/receive beam former circuitry, etc.). In some embodiments, at least a portion of the driver circuits 233 can be located at the base unit 110.

The base-unit electronics 240 include a CPU 242, input/out devices 243, and communication components 245. The CPU 242 includes a memory 248 and a programmable processor 249 configured to execute instructions in the memory 248 in order to perform various processes, logic flows, and routines. The input/out devices 243 can include, for example, the touchscreen 114, a camera 226, a microphone 227, and/or a speaker 228. The communication components 245 can include, for example, signal buses coupled to the wand port 111, the input controls 113a, the communication ports 113b, and the touchscreen 114. In several embodiments, the communication components 245 can further include a network adaptor, a wireless transceiver (e.g., Wi-Fi or cellular transceiver), or other suitable components for communication over the Internet, a computer network, and/or a wireless network.

In operation, the driver circuits 233 can operate the transducer array 232 to produce and steer an acoustic signal toward a target region of interest. The base-unit electronics 240, in turn, can drive the driver circuits 233 based on user input. For example, as described in greater detail below, the user can provide input by operating various graphical controls presented at the touchscreen 114. The driver circuits 233 can also produce information based on the acoustic signals returned to the transducer array 232, which the base-unit electronics 240 uses to display ultrasound images on the touchscreen 114 as the information is acquired.

As best seen in FIG. 2B, the transducer electronics 230 are powered by a first dedicated power source device, or first battery 254, and the base-unit electronics 240 are powered by a second dedicated power source device, or second battery 256. In the illustrated embodiment, both the first and second batteries 254 and 256 are located at the base unit 110. The first battery 254 can include, for example, a removable battery (e.g., the battery 122 of FIG. 1B), and the second battery 256 can include, for example, an internal battery. In one embodiment, the internal battery can be integrally coupled to the base-unit electronics 240. For example, a hardwire connection (not shown) can permanently or semi-permanently couple the internal battery with the base-unit electronics 240 such that the user cannot readily remove the internal battery from the base unit 110. In several embodiments, a capacitor can be used in lieu of the internal battery. As further shown in FIG. 2B, the processor 249 can be operably coupled to each of the batteries 254 and 256. For example, the processor 249 can communicate with an intermediary circuit (not shown) that detects charge level. As described in greater detail below, the processor 249 can also be coupled to a switch or switching circuit 258 that can connect the first and second batteries 254 and 256 to one another for charging the second battery 256 with the first battery 254.

In contrast to the portable system 100, conventional portable ultrasound systems do not employ multiple dedicated power sources. Rather, all of the electronics, including the transducer electronics, receive power from the same battery or same group of batteries. One challenge with this configuration is that the transducer electronics consume a substantial amount of battery power. If the batteries become fully depleted during an ultrasound scan, the portable system will shut down. In these scenarios, the user can lose data acquired from the ultrasound scan. Also, to continue ultrasound scanning, the user must recharge or replace the batteries, reboot the system, and then re-enter the scanning parameters before then can continue scan. This is not only an inconvenience, but it can create delays during patient examinations. In critical care situations, where time can be of the essence, a delay of even several seconds can be substantial. In addition, in many portable systems, a user can use the system not only to scan, but also to review ultrasound images acquired during a prior scanning session. For example, the user can review the images for establishing a particular diagnosis. However, if the batteries are depleted of charge, users can be inconvenienced because they must find new batteries or find a place at which they can plug the system in for recharging.

Embodiments of portable ultrasound systems configured in accordance with the various embodiments of the disclosure, however, address these and other limitations of conventional portable ultrasound systems. In one embodiment, the base-unit electronics 240 are configured to temporarily suspend an ultrasound scan when it detects that the battery life of the first battery 254 is low. When the charge in the first battery 254 is restored (e.g., when the first battery is replaced), the base-unit electronics 240 can immediately resume the ultrasound scan without having to reboot the base unit and without losing data. In one embodiment, the stored data can include the scanning parameters (e.g., gain, scan depth, frame rate, etc.) selected by the user before ultrasound scanning was suspended. In another aspect of this embodiment, when ultrasound scanning is suspended, the second battery 256 continues to power the other components of the base unit 110. As such, the base-unit electronics 240 still allow a user to view acquired images stored on the base unit 110 and/or carry out other functions. For example, in one embodiment, the user can still operate the base unit 110 to place or overlay a graphical marker on an acquired image. In another embodiment, the user can still operate the base unit 110 to use an email application, web browser, or other application provided by the base unit 110.

Figure 3A:
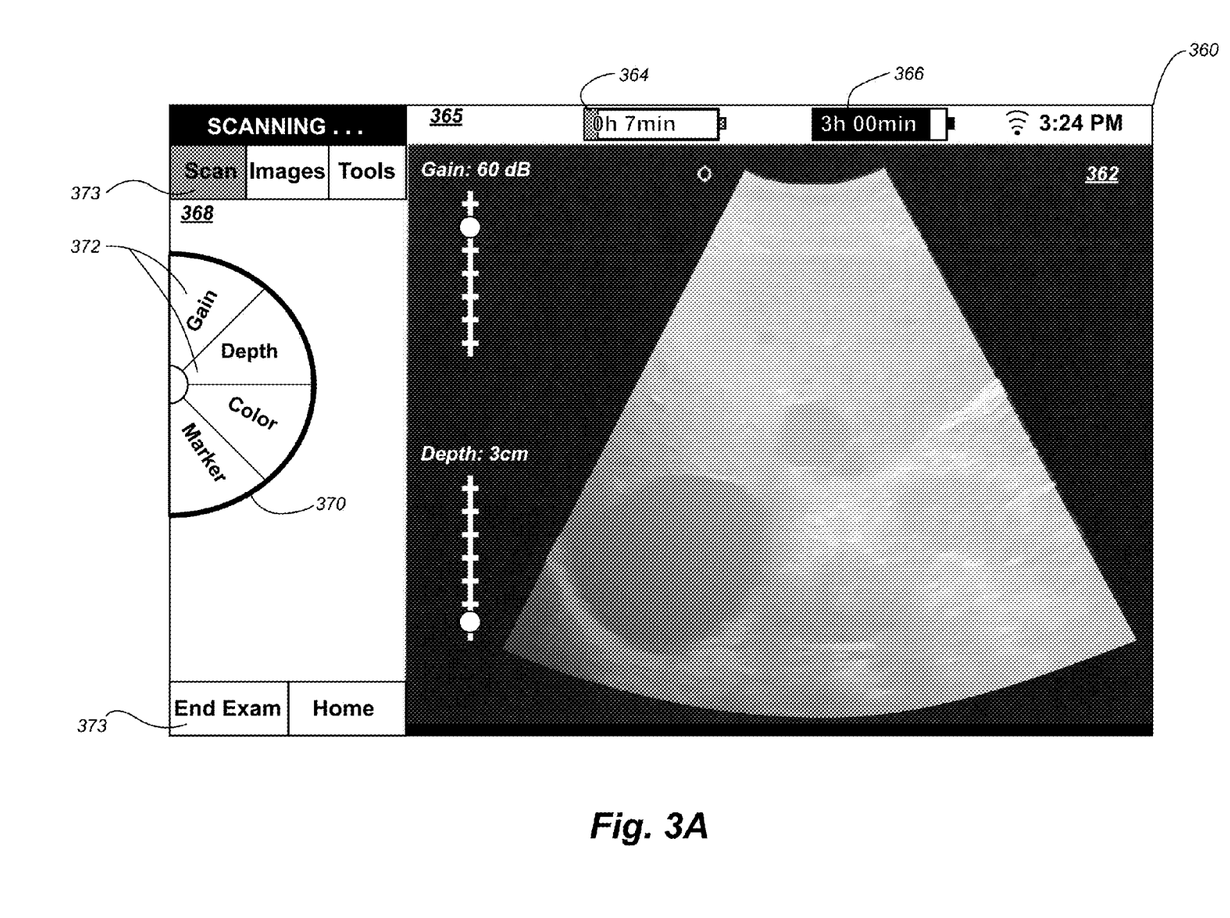
FIGS. 3A-3E show a graphical user interface presented at a touchscreen of a portable ultrasound system in accordance with several embodiments of the disclosure.

FIGS. 3A-3E show a graphical user interface 360 presented at the touchscreen 114 (FIG. 1A) in various display states in accordance with several embodiments of the disclosure. Referring first to FIG. 3A, the graphical user interface 360 includes an active image area 362 containing an ultrasound image, a status bar 365 (indicating time, wireless signal strength, etc.), and a control area 368. As shown, the status bar 365 indicates that the system is in a live scan mode and the active image area indicates that the transducer electronics 240 (FIG. 2A) are acquiring ultrasound information using a gain value of 60 dB and a scan depth of 3 cm (as indicated on the active image area 362). In addition, the active image area 362 displays ultrasound images as the processor processes the ultrasound information. As further shown in FIG. 3A, the status bar 365 contains a first battery icon 364 indicative of the remaining charge time of the first battery 254 (0 hours and 7 minutes in FIG. 3A) and a second battery icon 366 indicative of the remaining charge time of the second battery 256 (3 hours and 0 minutes in FIG. 3A).

In the illustrated embodiment of FIG. 3A, the control area 368 includes a number of touch-selectable controls, such as a thumbwheel 370 and soft buttons 372 located on the thumbwheel 370, and soft buttons 373 located off of the thumbwheel 370. In operation, the touch-selectable features enable users to control and adjust various scanning parameters of the ultrasound scan. For example, to initiate an ultrasound scan, a user can select the soft button labeled "Scan." To control the gain or scan depth parameters, the user can select soft buttons labeled "Gain" or "Depth," respectively. To change the scan mode to color power Doppler (CPD) mode, the user can select a soft button labeled "Color." In one embodiment, the control area 368 can include touch-selectable controls described, for example, in co-pending U.S. patent application Ser. No. 14/256,759, titled "Hand-Held Medical Imaging System with Thumb Controller and Associated Apparatuses and Methods," filed concurrently herewith and incorporated herein in its entirety by reference. In another embodiment, the control area 368 includes touch-selectable features that do not modify ultrasound scanning parameters. For example, the user can select the "Marker" soft button to position a graphical marker on the ultrasound image.

Figure 3B:
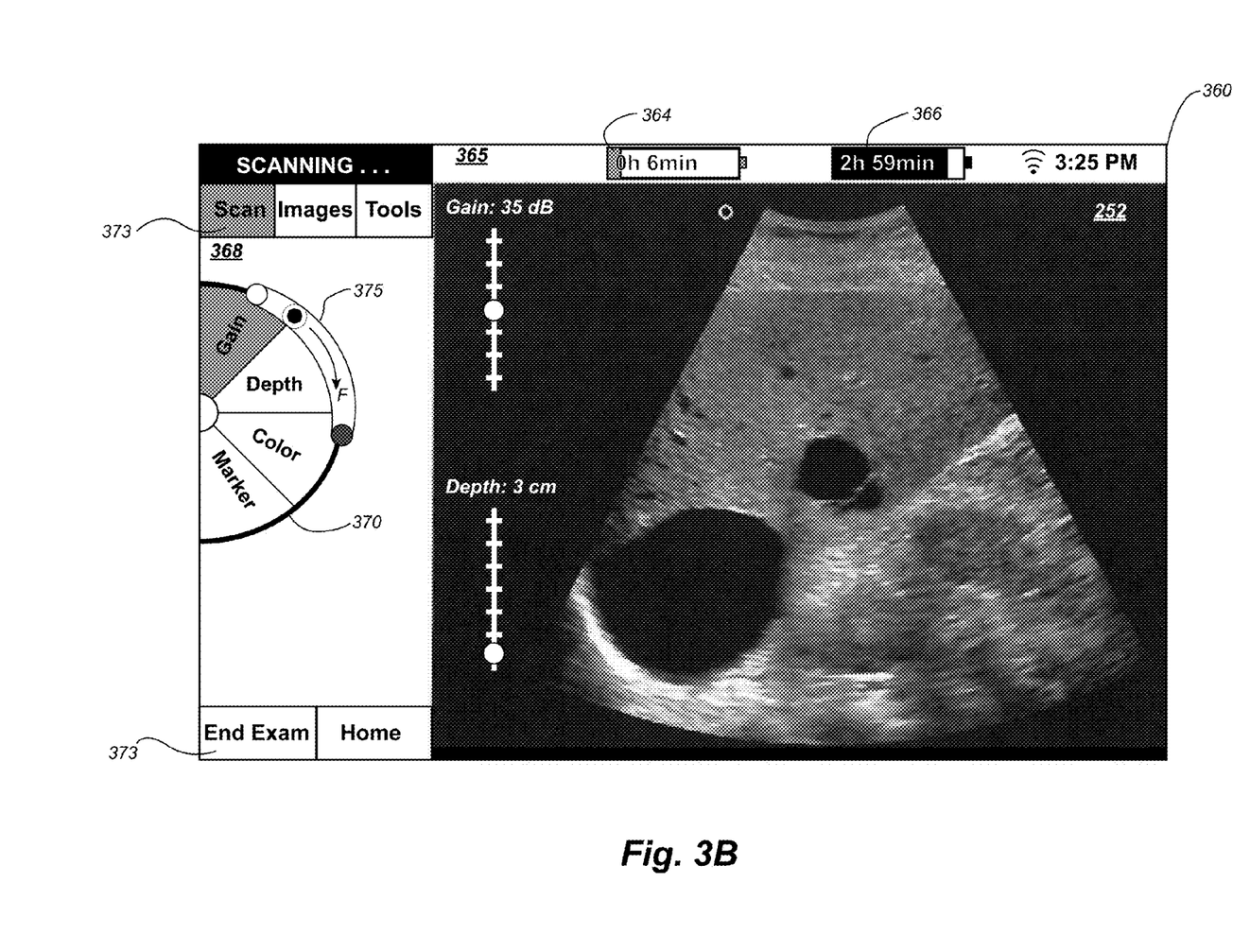

FIG. 3B shows the graphical user interface 360 in a configuration in which the user has selected the "Gain" button and the processor has displayed a slider feature 375 adjacent the thumbwheel 370. As shown, the user has operated the slider feature 374 (as shown by the arrow F) to decrease the gain from 60 dB to 35 dB. Also, the lifetime of the first and second batteries has decreased relative to the battery lifetimes shown in FIG. 3A (i.e., to 0 hours and 6 minutes for the first battery 254, and to 2 hours and 59 minutes for the second battery 256).

Figure 3C:
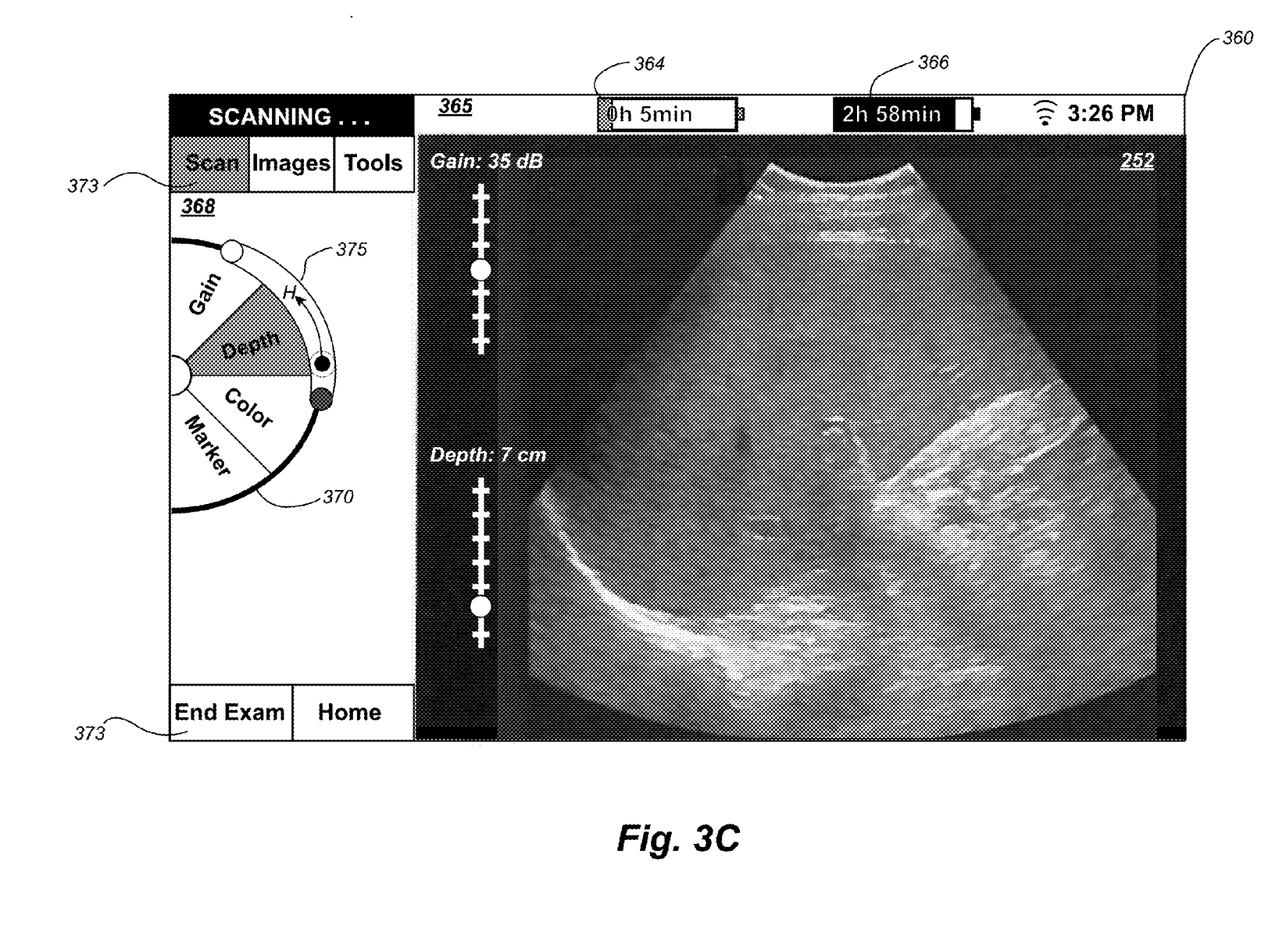

FIG. 3C shows the graphical user interface 360 in a configuration in which the user has selected the "Depth" button and the user has operated the slider feature 375 (as shown by the arrow H) to increase the scan depth from 3 cm to 7 cm. At the stage of FIG. 3C, the battery life of the first and second batteries 254 and 256 has further decreased relative to the battery lifetimes shown in FIG. 3B (i.e., to 0 hours 5 minutes for the first battery 254, and 2 hours and 58 minutes for the second battery 256). Also, an "X" is superimposed on the first battery icon 364 to indicated that the first battery 254 is at a the critical threshold level. For example, the threshold can correspond to a certain percentage of remaining charge relative to the overall charge capacity of the first battery 254 (e.g., about 2%, about 5%, or about 10% of the charge capacity). In several embodiments, the critical level can correspond to a threshold set by the manufacture and/or a threshold setting configured by the user of the device.

Figure 3D:
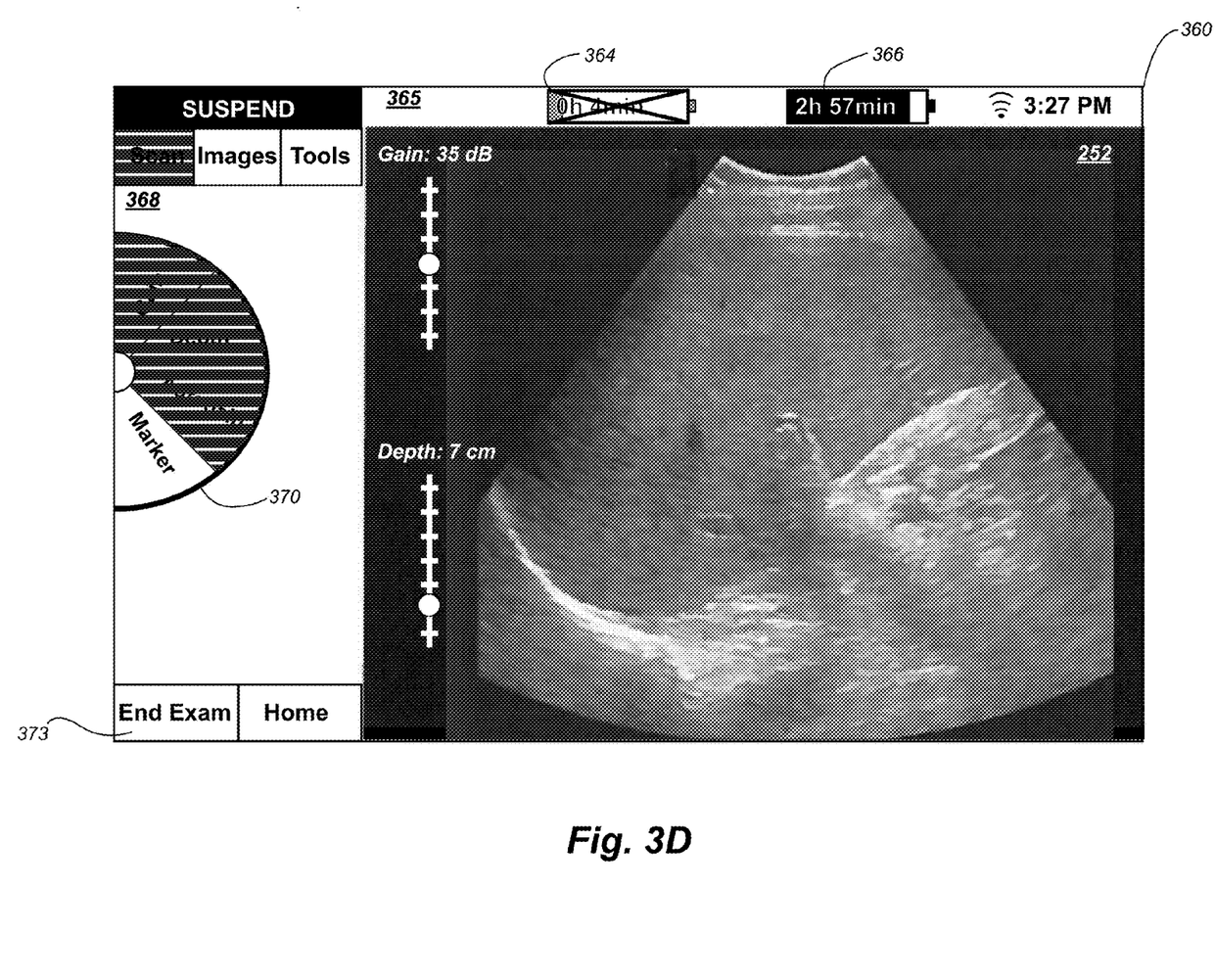

FIG. 3D shows the graphical user interface 360 in a configuration in which the processor has suspended the live scan in response to detecting that the first battery 254 has a remaining lifetime of less than 5 minutes. As shown, the processor has also disabled or deactivated the "Scan" soft button as well as the soft buttons on the thumbwheel 370 used to control the ultrasound scanning parameters (i.e., "Gain," "Depth," and "Color," but not "Marker"). In one aspect of this embodiment, other controls on the control area 368 can remain enabled. For example, the user can still select the "Images" soft button to view ultrasound images stored in the memory. Also, the user can select the "TOOLS" soft button to implement a graphical tool, such as a caliper tool or a graphical marker. In some embodiments, the user can select various graphical tools and other control features described in co-pending U.S. patent application Ser. No. 14/256,744, and titled "Hand-Held Medical Imaging System with Improved User Interface for Deploying On-Screen Graphical Tools and Associated Apparatuses and Methods," filed concurrently herewith and incorporated herein in its entirety by reference. In another embodiment described in greater detail below, the user can select the "HOME" soft button to access another application or program (e.g., an email application).

Figure 3E:
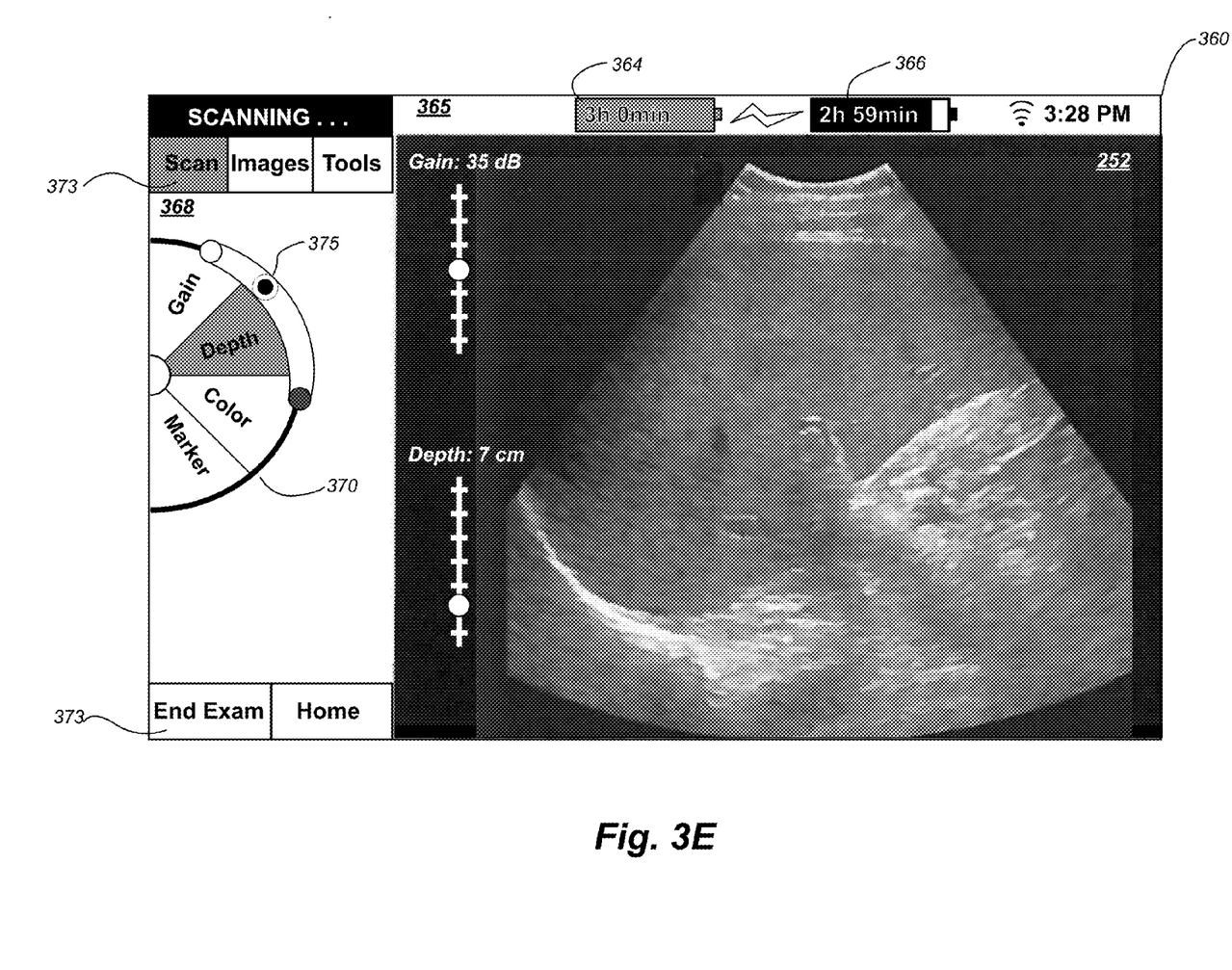

FIG. 3E shows the graphical user interface 360 in a configuration in which the user has replaced or recharged the first battery 254. As shown, the first battery icon 364 indicates that the first battery 254 is at a full charge level and has a lifetime of 3 hours and 0 minutes. In addition, the scanning session has been resumed, with the gain and depth parameters remaining at 35 dB and 7 cm, respectively. Also, and the thumbwheel 370 and the scan-related soft buttons have been restored or reactivated. In some embodiments, the charged or replaced first battery 254 can replenish the charge (e.g., top off) the charge of the second battery 256. In one embodiment, the first battery 254 can replenish the charge of the second battery 256 so long as the first battery 254 is above a certain charge level (e.g., 95% charge, 75% charge, 50% charge). For example, the processor can open and close the switch 258 (FIG. 2B) based on the charge level of the first battery 254. One advantage of this feature is that the user may only have to be concerned about recharging or replacing the first battery 254 since it automatically recharges the second battery 256. In the illustrated embodiment, the status bar 365 contains a charge indicator that can indicate that the first battery 254 is charging the second battery 256.

Figure 4:
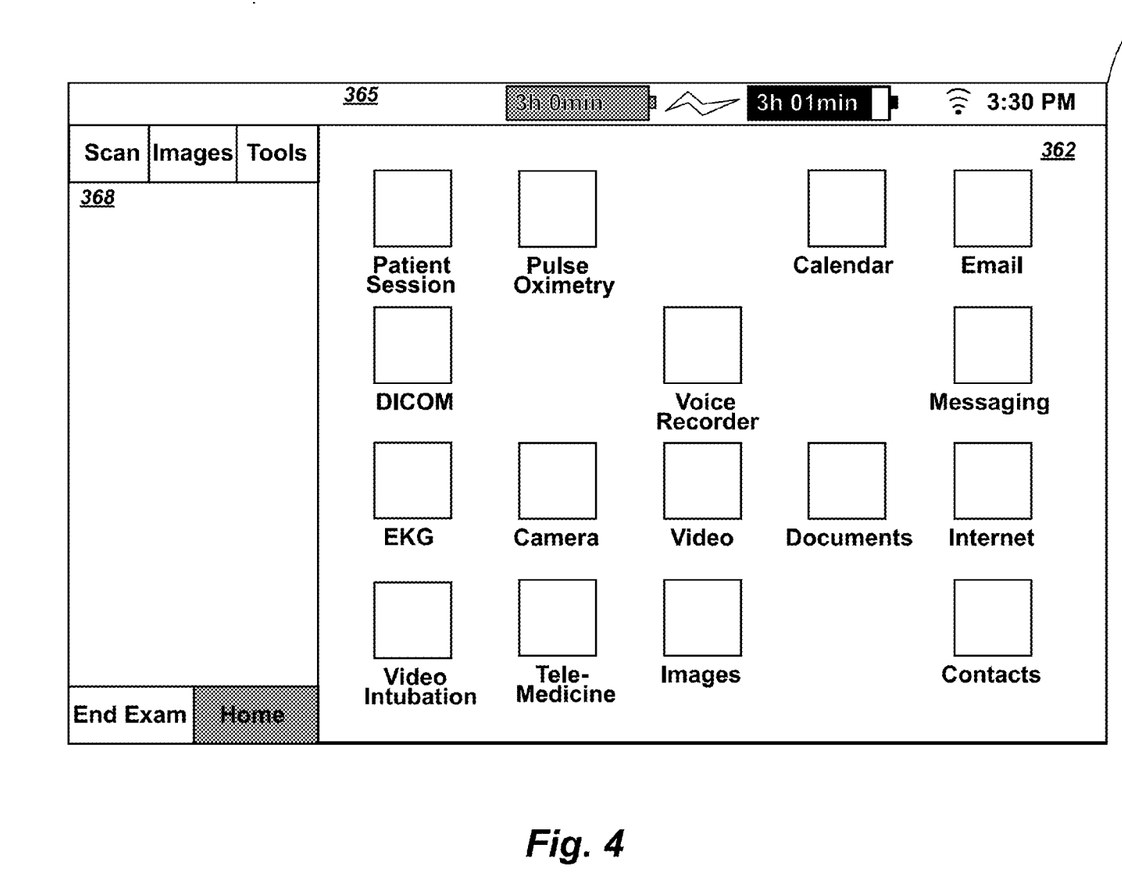
FIG. 4 is diagram showing a graphical user interface of a portable ultrasound system in accordance with an embodiment of the disclosure.

FIG. 4 is diagram showing the graphical user interface 360 displaying a home screen in the active image area 362 in accordance with an embodiment of the disclosure. In one embodiment, the user can access the home screen by selecting the "HOME" soft button shown in the graphical user interface of FIGS. 3A-3E. In this display state, the base unit 110 can operate in a manner similar to a smart phone, a personal digital assistant, or other similar device. When operating the base unit 110 in this manner, the user can disconnect the transducer wand 102. In addition, the user can remove the first battery 254 to reduce the weight of the base unit 110 and to thereby make it even more portable.

As shown, the processor can present a number of icons in the active image area 362. The icons can correspond, for example, to a program (e.g., an application), a folder, a file, etc. In use, a user can use select these icons to access e-mail, documents, images, video, and/or Internet services; participate in a video session; and/or communicate (e.g., wirelessly communicate) with a remote computing device (e.g., another user device, a remote server, etc.). For example, in some embodiments the user can connect to a secure medical server from the home screen, e.g., a digital imaging and communications in medicine (DICOM) server. The DICOM server can allow the user to access, update, or otherwise interact with a patient's medical record, such as to append an ultrasound image or clip to a patient's medical record. The base unit 110 can also support other applications, such as pulse oximetry, electrocardiography (EKG), video intubation.

In another aspect of this embodiment, a user can access the home screen to initiate a remote session (e.g., a video session) with a remote party, such as a colleague (e.g., a doctor or clinician at a different hospital), a technician or support person (e.g., an instructor at a remote learning facility), or other remote individual. In one embodiment, the user and the remote party can simultaneously view ultrasound images (frozen or live) on the active image area 462. For example, the remote party can help assess or interpret the ultrasound image. In another embodiment, the user can employ the camera 226 (FIG. 2A) to provide video feedback to the remote party for training or coaching purposes. For example, the remote party can remotely observe the user operating the transducer wand 102 (FIG. 1A) to coach the user on proper use or positioning of the transducer wand 102.

In some embodiments, the processor can display ultrasound and other images on a remote display, such as a large-screen monitor, via a graphical remote control displayed at the control area 368 and/or the active image area 362. For example, the processor can establish a wireless link (e.g., a Bluetooth, WiFi, etc.) with a remote display that allows the base unit 110 to transmit the ultrasound image to the remote display. In several of these embodiments, the processor can present a graphical remote or other controller that allows the user to navigate or otherwise manipulate the image on the remote display.

In a further embodiment, the base unit 110 can support an application program interface (API) that allows user as well as third parties to develop and support their own ultrasound applications. For example, the API can allow a third party to create and offer a teaching tool for instructing others how to carry out a particular type of ultrasound scan. Such an application could be available for purchase and/or be offered as an integrated part of a course curriculum or learning module.

Figure 5:
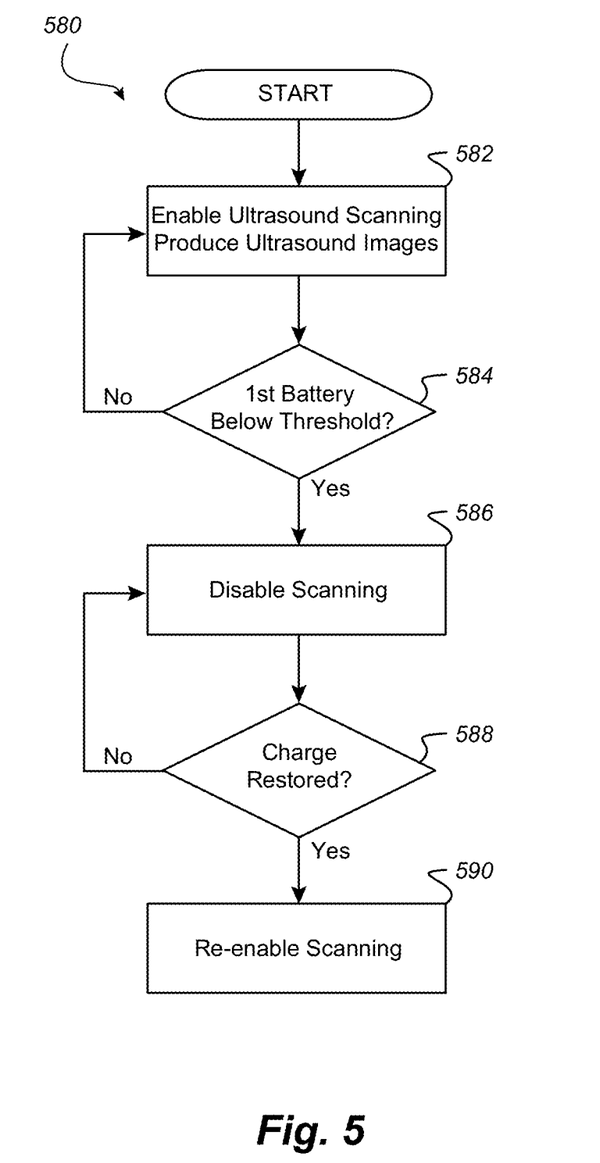
FIG. 5 is a flow diagram illustrating a routine for powering a portable ultrasound system in accordance with an embodiment of the disclosure.

FIG. 5 is a flow diagram illustrating a routine 580 for powering a portable ultrasound system in accordance with an embodiment of the disclosure. After the start block, the routine 580 proceeds to enable ultrasound scanning. For example, the routine 580 can begin when the user presses the "Scan" soft button shown in FIG. 3A. Once enabled, the base-unit 110 can begin to produce ultrasound images corresponding to the ultrasound information it receives from the transducer electronics 240. As discussed above, the user can control the scan at this stage by modifying various scanning parameters (e.g., gain, scan depth, etc.). The routine 580 then proceeds to decision block 584 to monitor the first battery 254.

At decision block 584, the routine detects the charge level of the first battery and determines if it below a threshold. For example, the threshold can correspond to a percentage level of charge (e.g., ~0%, 1%, 5%, or 15% of the remaining charge). In addition or alternately, the threshold can be based on certain minimum battery lifetime (e.g., 1, 2, or 5 minutes of minimum lifetime). If the charge level is below the charge storage threshold, the routine 580 proceeds to block 586, otherwise the routine 580 returns to block 582 to continue ultrasound scanning.

At block 586, once the routine detects that the first battery is below the threshold, the routine suspends live scanning. For example, the processor can send a signal to the transducer electronics 230 to enter a standby state (e.g., a power conservation state) or to shut down. Also, as discussed above, the processor can disable certain controls at the touch screen 114 and/or store data in the memory, such as the ultrasound scanning parameters selected by the user. In various embodiments, the routine 580 can automatically suspend live scanning when the first battery 254 is below the threshold. In other embodiments, however, the routine 580 can suspend live scanning by prompting the user to suspend scanning. In cases where the user opts not to suspend scanning, the live scan may continue until the first battery 254 is fully depleted of charge.

At block 588, the routine monitors the charge level to detect whether the first battery 254 has been charged or replaced. If charge is restored above the threshold, processing continues to block 590, at which point the routine 580 can resume the ultrasound scanning session. For example, the routine 580 can resume the ultrasound scan based on the scanning parameters stored in the memory at block 586. In some embodiments, the routine 580 can control internal connection with the base unit 110 (e.g., the switch 258) such that the first battery 254 replenishes the charge of the second battery 256, as discussed above. In several such embodiments, the first battery 254 can have a substantially larger charge capacity such the second battery 256 does not draw a significant amount of power from the first battery 254 when the second battery 256 is being replenished.

From the foregoing, it will be appreciated that specific embodiments of the disclosure have been described herein for purposes of illustration, but that various modifications may be made without deviating from the scope of the various embodiments of the disclosure. Moreover, because many of the basic structures and functions of transducer arrays, transducer electronics, and other processor electronics are known, they have not been shown or described in further detail to avoid unnecessarily obscuring the described embodiments. Further, while various advantages and features associated with certain embodiments of the disclosure have been described above in the context of those embodiments, other embodiments may also exhibit such advantages and/or features, and not all embodiments need necessarily exhibit such advantages and/or features to fall within the scope of the disclosure.

The invention claimed is:

1. A portable ultrasound system, comprising:
   transducer electronics; and
   a base unit, including—
      base-unit electronics configured to receive user input and to operate the transducer electronics to perform ultrasound scanning based on the user input,
      a first power source device configured to power the transducer electronics, and
      a second power source device configured to power the base-unit electronics without powering the transducer electronics.

2. The portable ultrasound system of claim 1 wherein:
   the first power source device is removably coupled to the base unit; and
   the second power source device is fixedly coupled with the base-unit electronics.

3. The portable ultrasound system of claim 2 wherein:
   the first power source device includes a rechargeable battery; and
   the second power source device includes an integrated capacitor.

4. The portable ultrasound system of claim 1 wherein the base-unit electronics include:
   a memory for storing a number of program instructions; and
   a processor configured to execute the instructions, in order to:
      detect that the first power source device has a charge level that has fallen below a threshold,
      temporarily disable ultrasound scanning without powering down the base-unit electronics in response to detecting the charge level has fallen below the threshold,
      detect that charge has been restored to a level above the threshold, and
      re-enable ultrasound scanning in response to detecting the restored charge.

5. The portable ultrasound system of claim 4 wherein the processor is configured to execute further instructions stored in the memory, in order to:
   modify one or more ultrasound scanning parameters based on the user input,
   store the modified scanning parameters in the memory in response to detecting the charge level has fallen below the threshold; and
   resume the ultrasound scanning using the modified scan parameters stored in the memory in response to detecting that ultrasound scanning is re-enabled.

6. The portable ultrasound system of claim 5 wherein the ultrasound scanning parameters includes at least one of gain and depth.

7. The portable ultrasound system of claim 1 wherein the base-unit electronics include:

a memory for storing a number of program instructions; and
a processor configured to execute the instructions, in order to:
  detect that the first power source device has a low charge or no charge,
  detect that the first power source device has been recharged or replaced;
  recharge the second power source device with power provided from the recharged or replaced first power source device.

8. A portable ultrasound system, comprising:
a transducer wand; and
a base-unit operably coupled to the transducer wand to perform an ultrasound scan, wherein
  the base unit includes—
  base-unit electronics,
  a first battery that provides dedicated to power to the transducer wand,
  a second battery that provides dedicated power to the base-unit electronics.

9. The portable ultrasound system of claim 8 wherein the base unit includes a compartment containing the first battery, and wherein the second battery is located outside of the battery compartment.

10. The portable ultrasound system of claim 8 wherein the transducer wand includes:
  a transducer array powered by the first battery; and
  a driver circuit powered by the first battery to drive the transducer array.

11. The portable ultrasound system of claim 10 wherein the driver circuit includes one or more analog amplifiers and one or more analog-to-digital converters operably coupled to the analog amplifiers.

12. The portable ultrasound system of claim 8 wherein the base-unit electronics are configured to detect a charge level of the first power source device and to temporarily disable the ultrasound scan based on the detected charge level without powering down the base-unit.

13. The portable ultrasound system of claim 8 wherein:
  the base unit further includes a display; and
  the base-unit electronics are configured to:
    display one or more ultrasound images on the display based on information acquired by the transducer electronics during the ultrasound scan, and
    continue to display the ultrasound images when the first battery has zero charge.

14. The portable ultrasound system of claim 13 wherein the base unit electronics are further configured to display the ultrasound images when only the second battery is installed in the base unit electronics.

* * * * *